United States Patent [19]

Hokanson

[11] Patent Number: 4,532,933
[45] Date of Patent: Aug. 6, 1985

[54] FOCUSING MECHANISM FOR AN ULTRASOUND DEVICE

[76] Inventor: D. Eugene Hokanson, 3324 - 72nd Ave. Southeast, Mercer Island, Wash. 98040

[21] Appl. No.: 487,934

[22] Filed: Apr. 25, 1983

[51] Int. Cl.³ .............................................. A61B 10/00
[52] U.S. Cl. ..................................... 128/660; 128/663; 73/642
[58] Field of Search ...................... 128/660, 661, 663; 73/861.25, 642, 644

[56] References Cited

U.S. PATENT DOCUMENTS

| | | | |
|---|---|---|---|
| 3,927,662 | 12/1975 | Ziedonis | 128/660 |
| 4,097,835 | 6/1978 | Green | 128/663 X |
| 4,217,516 | 8/1980 | Iinuma et al. | 128/660 X |
| 4,237,729 | 12/1980 | McLeod et al. | 128/663 X |
| 4,325,381 | 4/1982 | Glenn | 128/660 |
| 4,327,738 | 5/1982 | Green et al. | 128/660 |
| 4,355,643 | 10/1982 | Laughlin et al. | 128/663 |
| 4,387,720 | 6/1983 | Miller | 128/660 |

*Primary Examiner*—Kyle L. Howell
*Assistant Examiner*—Francis J. Jaworski
*Attorney, Agent, or Firm*—Ward Brown; Robert W. Beach

[57] ABSTRACT

Side-by-side transmitting and receiving transducers of a medical Doppler ultrasound device are covered by a converging lens of synthetic rubber material through which the speed of ultrasound waves is slower than the speed of the waves in soft body tissue. The lens has a planar inner face butted against the planar transmitting and receiving faces of the transducers and a convexly curved outer face including two portions each extending over both transducers, one of such portions being smaller and more sharply curved than the other. The composite lens focuses the transmitted ultrasound waves in two zones overlapping in range so that the same transducer arrangement can be used in obtaining velocity information from deep or shallow blood vessels.

13 Claims, 9 Drawing Figures

FOCUSING MECHANISM FOR AN ULTRASOUND DEVICE

BACKGROUND OF THE INVENTION

1. Field of the Invention

The present invention relates to medical ultrasound devices having transmitting transducers for beaming ultrasound waves into the body and adjacent receiving transducers for detecting the ultrasound waves reflected from internal body matter. More specifically, the present invention relates to ultrasound focusing mechanism for maximizing the reflected waves detected by the receiving transducer which waves were reflected from matter within a focal zone located a desired distance from the transducers.

2. Prior Art

In a medical Doppler ultrasound device, a transmitting transducer beams ultrasound waves of a known frequency into the body. A receiving transducer closely adjacent and stationary relative to the transmitting transducer detects waves reflected from internal body matter. The object is to detect waves reflected from matter, such as blood corpuscles, moving toward or away from the side-by-side transducers. In accordance with the well-known Doppler effect, the difference in frequency of a wave before and after reflection indicates the velocity of the matter from which the wave was reflected relative to the wave transmitter. A major use for medical Doppler ultrasound devices is to detect average blood velocity or, with the use of a frequency spectrum analyzer, the range of instantaneous velocities through a blood vessel. For such Doppler devices, only received waves having frequencies different from the frequency of the transmitted waves are of interest.

In medical "scanning" ultrasound devices, the object is to reflect transmitted ultrasound waves off stationary or substantially stationary internal body parts, to detect the reflected waves and to process a corresponding electrical signal to provide an image of the internal body part in plan or in section. Because the frequency of waves reflected from stationary or substantially stationary body parts will be the same or about the same as the frequency of the transmitted waves, only waves having a frequency close to the transmission frequency are of interest.

In a scanning device, the transmitted beam of ultrasound waves must be narrow in the area of the body part being scanned for a high quality image to be generated. A concave epoxy lens has been used to reduce the divergence of the transmitted beam and assist in creating a "zone of maximum intensity" or "focal zone" within which the beam is sufficiently narrow. The length and location of the focal zone also depends on the sizes of the transducers because only small transducers can be used to transmit beams that are narrow in an area close beneath the skin of the patient. Further, the transmission frequency affects the length and location of the focal zone because high frequency beams are less divergent but, unfortunately, attenuate more rapidly than low frequency beams.

Different transducers are used in the scanning devices depending on the depth of the body part being scanned. A transducer 6 millimeters in diameter and having a transmission frequency of 5 to 7.5 megahertz is typical of those used for scanning body parts 1 to 3 centimeters below the skin; a transducer 10 to 13 millimeters in diameter and having a transmission frequency of 3.5 megahertz is typical of those used for scanning body parts 4 to 10 centimeters below the skin; and a transducer 19 millimeters in diameter and having a transmission frequency of 2.25 megahertz is typical of those used for scanning body parts 7 to 19 centimeters below the skin.

Up until the present invention, focusing lenses had not been used in the medical Doppler ultrasound devices. Rather, different transducers were used depending on the depth of the blood vessel for which velocity information was desired, which usually is in the range of about 10 millimeters to 60 millimeters below the skin. In general, the transducers used for deep blood vessels were larger and of lower frequency than the transducers used for superficial vessels.

The required ability to accept a variety of transducers of different frequencies complicates the remainder of the medical Doppler ultrasound device. In addition, the output of the device is often an audible signal from a loudspeaker or headphones and the pitch and pattern of the signal is interpreted by the operating technician. Changing from a transducer of one frequency to a transducer of a different frequency changes the pitch of the output and can complicate interpretation of the output.

SUMMARY OF THE INVENTION

The principal object of the present invention is to provide an improvement for the transducers of a medical Doppler ultrasound device which improvement allows the same transducers to be used in obtaining velocity information from both deep and shallow body matter.

It also is an object to provide such improvement in a form which allows the use of conventional transducers having planar transmitting and receiving faces without interfering with positioning the transducers over the area from which velocity information is desired and without interferring with consistent reliable transmission of ultrasound waves into the body.

The foregoing objects can be accomplished by providing a converging lens for refracting ultrasound waves transmitted and received by the transducers of the medical Doppler ultrasound device. More specifically, such objects can be accomplished by a lens having at least two portions of different curvature each extending over both transmitting and receiving faces of the transducers, such lens preferably being formed of a material in which the speed of the ultrasound waves is slower than in body tissue so that the inner face of the lens can be planar and butted against the planar transducer faces and the outer face of the lens can be convex for focusing the ultrasound waves. Preferably the more gradually curved portion of the lens is larger than the more sharply curved portion, and both lens portions are formed on the external surface of the lens.

DETAILED DESCRIPTION

Figure 1:
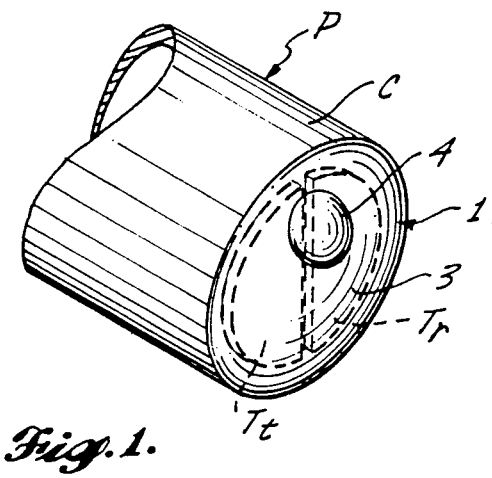
FIG. 1 is a fragmentary top perspective of the leading end portion of a transducer-carrying probe of a medical Doppler ultrasound device of the type with which the present invention is concerned, showing the focusing mechanism of the present invention covering the leading end of such probe.
Figure 3:
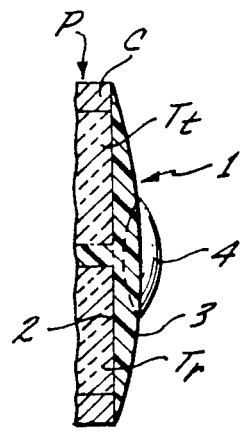
FIG. 3 is a fragmentary section taken along line 3—3 of FIG. 2.

The focusing mechanism of the present invention is intended to be used with the otherwise conventional transducer-carrying probe of a medical Doppler ultrasound device. The leading end portion of a representative probe P is shown diagrammatically in FIGS. 1 through 4. Such probe has a cylindrical outer case C. A pair of side-by-side piezoelectric ceramic transducers is carried inside the case toward its leading end and includes a transmitting transducer $T_t$ and a receiving transducer $T_r$. Each transducer is substantially semicylindrical and of a radius between about 6 millimeters and about 13 millimeters, preferably about 7.5 millimeters. The flat edges of the transducers are spaced apart for electrically and mechanically isolating the transducers from each other.

The transmitting transducer is driven by a suitable oscillator such that ultrasound waves of substantially constant frequency are transmitted from its outer end or face. Such frequency can be in the range of about 1 megahertz to about 10 megahertz but, in the present invention, preferably is about 5 megahertz.

In general, the leading end of the probe is placed in contact with the skin of a patient over the area for which velocity information is desired, such as over a blood vessel about 10 to 60 millimeters below the skin, so that the waves transmitted by transducer $T_t$ are beamed into the body. Such waves are reflected from internal body matter such as moving blood corpuscles. Some of the reflected waves impinge on the outer end or face of the adjacent receiving transducer $T_r$ causing a corresponding electrical signal to be generated which is processed and analyzed by the Doppler ultrasound device. The device generates a velocity-indicating output which is evaluated by the operating technician. Such output can be a chart record showing average blood velocity, or a trace or series of traces on a video monitor, or an audible signal from a loudspeaker or headphones, or a combination of such outputs.

In accordance with the present invention, the transmitting and receiving faces of the transducers are covered by an ultrasound converging lens 1. Preferably such lens has a planar inner face 2 butted against the outer faces of the transmitting and receiving transducers which preferably are also planar. The outer face of the lens is curved to achieve the desired convergent refraction of the ultrasound waves. As discussed further below, preferably the lens is formed of a material through which the speed of ultrasound waves is slower than through soft body tissue, in which case the outer face of the lens will be convex as shown in the drawings to refract the waves inward as they pass from the lens into the body.

Figure 4:
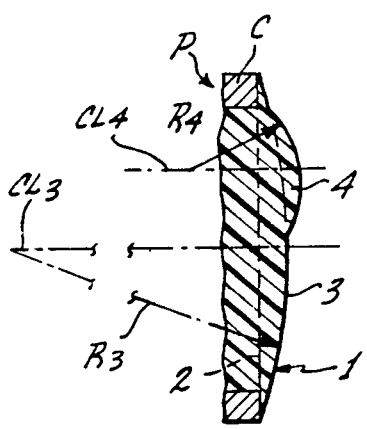
FIG. 4 is a fragmentary section taken along line 4—4 of FIG. 2.
Figure 2:
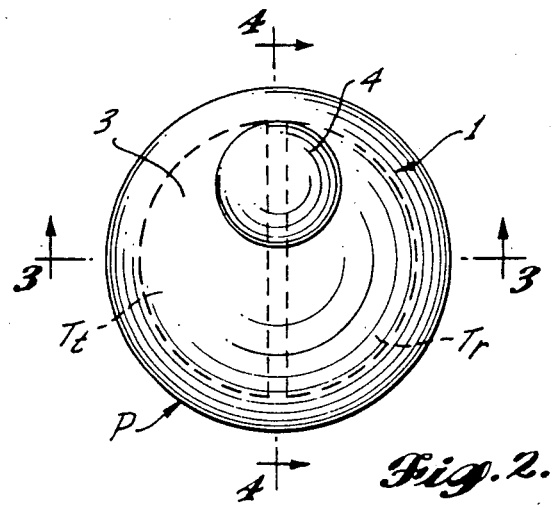
FIG. 2 is a front elevation of the probe of FIG. 1.

The outer face of lens 1 has two convexly and smoothly curved portions 3 and 4, respectively. Lens portion 3 preferably constitutes the major portion of the area of the outer lens face and preferably has a substantially constant radius of curvature $R_3$, as indicated in FIG. 4. Such portion of the lens constitutes the segment of a sphere having a radius much larger, preferably at least twice as large, as the radius of a transducer. Lens portion 4 forms a smaller, rounded protrusion which preferably has an outer face of substantially constant radius of curvature $R_4$, as indicated in FIG. 4, much smaller than the radius of curvature $R_3$ of lens section 3. Both lens portions are centered over the two transducers, that is, the lens portions are arranged with a common diametral plane which is located midway between and parallel to the planar facing edges of the semicylindrical transducers. The convexly curved outer face of each lens portion extends partly over each transducer.

The center lines $CL_3$ and $CL_4$ of the respective lens portions are shown in FIG. 4. Transmitted waves passing through the outer margin of lens portion 3 are refracted inward toward center line $CL_3$ to a greater degree than those passing through the inner portion of such lens portion. The effect is to focus such transmitted ultrasound waves toward the center line $CL_3$ and create a first focal zone of substantial length at a distance from the transducers. Body matter in such zone on or close to center line $CL_3$ will reflect the transmitted ultrasound waves back toward the transducer-carrying probe and, more specifically, back toward the outer face of the receiving transducer. Reflected waves passing through the outer margin of lens portion 3 are refracted inward at a greater angle than are reflected waves passing through the inner portion of such lens portion. Ideally, the reflected waves are refracted inward so as to impinge on the outer face of the receiving transducer at right angles.

Similarly, the effect of the smaller lens portion 4 is to refract transmitted waves inward toward the center line $CL_4$ but, because of the smaller radius of curvature of the smaller lens portion, transmitted waves passing through it are refracted inward at a greater angle than waves passing through the larger lens portion 3. This creates a second focal zone of substantial length closer to the transducers. Waves reflected from matter in such second focal zone and on or near the center line $CL_4$ pass through the portion of lens section 4 overlying the receiving transducer and are refracted inward to impinge on its outer face at right angles.

Experiments were conducted both for the purpose of finding an acceptable lens material and for determining preferred dimensions and proportions for the two lens portions. The room temperature vulcanizable (RTV) silicone rubber material designated "Type E" by Dow Corning Corporation of Midland, Mich. and promoted by that company for use as a mold making material was found to be effective in conveying ultrasound waves from an ultrasound transducer to the body. Additional testing established that the speed of ultrasound waves through such material is about 1400 meters per second, substantially slower than the generally accepted speed range of about 1520 meters per second to 1580 meters per second of ultrasound waves through soft body tissue. Accordingly, a converging lens of such material could be formed with a planar inner face and a convexly curved outer face. Alternatively the outer face could be planar and the inner face convex, or both faces could be convex.

The Dow Corning "Type E" material is substantially softer than the epoxy materials used in making lenses for the known ultrasound scanning devices. The relative softness of the material in combination with the convex outer face allows consistent, firm contact of the outer face of the lens with the skin of a patient so as not to interfere with consistent and uniform transmission of the ultrasound waves into the body. In contrast, the hard epoxy lenses used in the scanning devices often have concave outer faces because the speed of ultrasound waves through such lenses is faster than through soft body tissue, and it can be difficult to achieve consistent firm contact of the skin in the depression of the lens. An air gap between the lens and the skin can prevent transmission of the ultrasound waves into the body.

The Dow Corning "Type E" material is acceptable in all respects and is the preferred material for the focusing mechanism of the present invention.

In a second series of tests, converging lenses having different radii of curvature were formed of the Dow Corning "Type E" material without the smaller protruding lens portion 4 in order to establish the preferred radius of curvature for the larger lens section 3. A mold for each lens was formed by coating a ball having the desired radius with a separating agent and pressing the ball into a container of unhardened epoxy mold material. After the epoxy material had hardened, the ball was removed and the depression of the epoxy resin mold filled with the Dow Corning "Type E" material. Before hardening of such material the leading end of the transducer-carrying probe supplied with the model "CW-1" Doppler device manufactured by D. E. Hokanson, Inc. of Issaquah, Wash. was pressed into the mold and the lens material allowed to set in contact with the probe to secure the lens to the probe leading end. The leading end portion of the probe of the "CW-1" device is substantially as shown in FIGS. 1 through 4 with the external diameter of the casing C being about 10 millimeters and the diameter of the circle defined by the peripheries of the two side-by-side transducers $T_t$ and $T_r$ being about 7.5 millimeters. The ultrasound transmission frequency of that device is about 5 megahertz.

The lensed probe then was tested by aiming it at a steel ball of a diameter of 8.7 millimeters centered on the probe axis. To approximate conditions in the body, the ball and the leading end of the probe were submerged in water because the speed of ultrasound waves in water is about 1500 meters per second which is quite close to the speed of the waves through soft body tissue. The intensity of all reflected waves detected by the receiving transducer was plotted as a function of the distance between the transducers and the ball.

Figure 6:
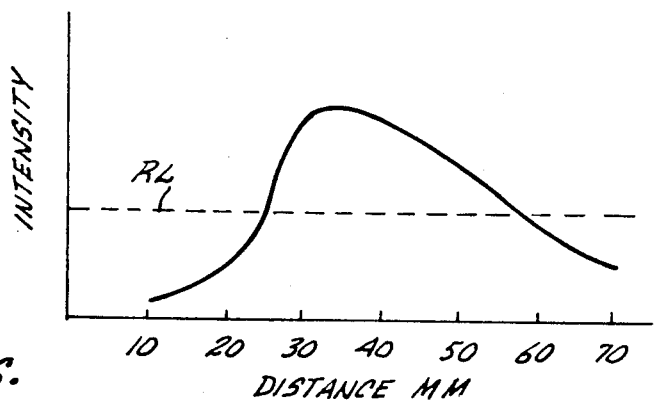
FIGS. 6, 7, 8 and 9 are corresponding graphs indicating the results of experiments conducted with different embodiments of focusing mechanism in accordance with the present invention.

The graph of FIG. 6 illustrates the results of the tests conducted for a lens having a constant radius of curvature of about 15.9 millimeters. An arbitrary reference line RL has been added and it will be noted that the detected intensity is above the line for the range of about 23 to about 60 millimeters. The lens with this radius of curvature created the desired focal zone for the larger lens section 3.

The next step was to establish the preferred size and radius of curvature for the lens portion 4. Several epoxy resin molds were constructed by the technique described above, each having the 15.9 millimeter radius of curvature. An additional depression was machined into each mold to test different sizes and radii of curvature for the lens section 4. Since the object of the lens portion 4 is to create a second focal zone closer to the transducers, a smaller radius of curvature was required; and since the ultrasound waves would have a shorter distance to travel and would be subject to less attenuation, the surface area of such lens portion should be substantially smaller than the surface area of the more gradually curved section 3.

Figure 7:
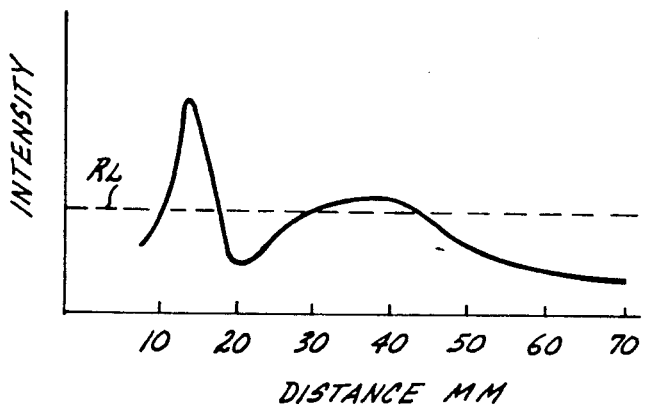

The graph of FIG. 7 shows the results of tests conducted when the more sharply curved, smaller convex lens portion 4 was added to the lens for which the results are shown in FIG. 6. The radius of curvature of the smaller portion was about 6.35 millimeters, and the width of such portion was about 5.5 millimeters. As expected, a second focal zone was created, as indicated by the intensity peak centered at about 15 millimeters. As also expected, the intensity level of the other intensity peak centered at about 40 millimeters was reduced because less than all of the ultrasound waves were beamed through the larger lens portion. The detected intensity of the reflected waves is above the reference line RL for the ranges of about 10 to 20 millimeters and about 30 to 45 millimeters.

Figure 8:
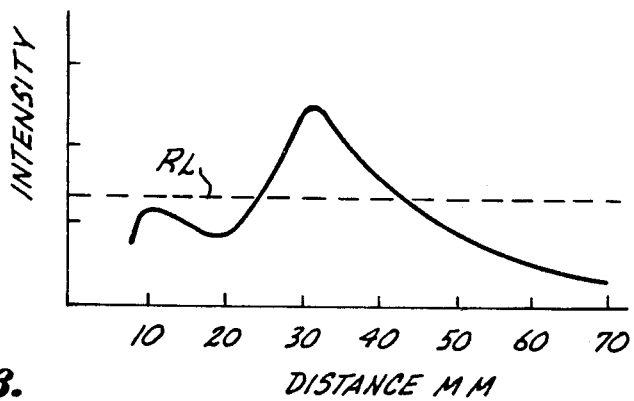

The graph of FIG. 8 shows the results of tests conducted when the radius of curvature of the smaller lens portion was reduced to shift its focal zone closer to the transducers. The width of such portion also was reduced to decrease the height of its intensity peak and, correspondingly, increase the height of the intensity peak for the larger lens portion. The radius of curvature of the smaller portion was about 3.2 millimeters and the width of such portion was about 2.5 millimeters. The intensity of the detected reflected waves is above the reference line RL for the range of about 23 millimeters to about 42 millimeters. In addition, the valley between the two intensity peaks is quite shallow, indicating that the two focal zones overlap in range.

Figure 9:
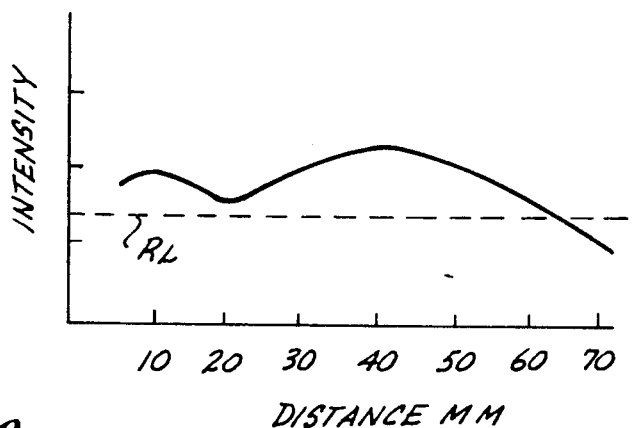

In the next set of tests the same radius of curvature was used for the smaller lens portion, namely about 3.2 millimeters, but its width was increased to 3.8 millimeters to raise the height of its intensity peak and decrease the height of the intensity peak for the larger lens portion. As shown in FIG. 9, this change resulted in the intensity of the detected reflected waves being above the reference line RL for the entire preferred range of less than 10 millimeters to greater than 60 millimeters. A lens having these dimensions has in fact been incorporated in the model "CW-1" Doppler device which has been found to be effective in obtaining blood velocity information from both superficial and deep blood vessels.

Figure 5:
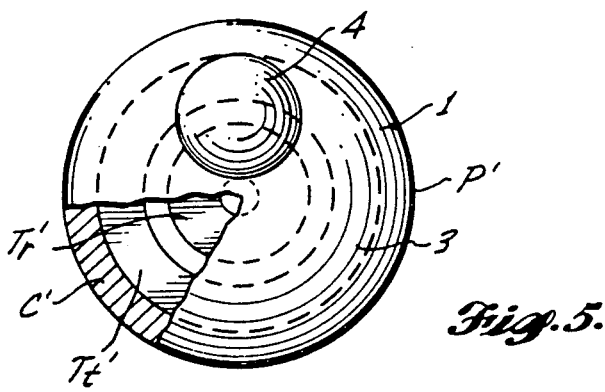
FIG. 5 is a front elevation of a second form of transducer-carrying probe in which the present invention can be used.

The focusing mechanism of the present invention can be used with transducer arrangements other than the side-by-side semicylindrical arrangement shown in FIGS. 1 through 4. For example, FIG. 5 shows another commonly used arrangement of transducers in which the probe P' has a cylindrical outer casing C' carrying annular, concentric transmitting and receiving transducers $T_t'$ and $T_r'$. The lens 1 of the present invention shown in FIG. 5 is identical to the lens shown in FIGS. 1 through 4. The planar inner face of the lens is butted against the planar transmitting and receiving faces of the transducers. The larger lens portion 3 extends over both the transmitting and receiving transducers. The smaller, more sharply curved lens portion 4 is centered over the gap between the transducers so as to extend partly over each of them. As in the first described embodiment of the invention, the effect of the composite lens is to focus the ultrasound waves transmitted by transducer $T_t'$ at different distances and create two focal zones preferably overlapping in range; and to refract waves reflected from body matter in such zones to impinge on the outer face of the receiving transducer $T_r'$.

I claim:

1. In focusing mechanism for a medical Doppler ultrasound device having first transducer means for transmitting ultrasound waves into the body toward internal body matter spaced from such transducer means and second transducer means for receiving at least some of the transmitted ultrasound waves reflected from such internal body matter, the first and second transducer means being positioned in closely adjacent relationship with a space therebetween and having respective planar outer transmitting and receiving faces, the improvement comprising converging lens means having an internal face with planar portions butted against the planar outer faces of the first and second transducer means, respectively, said lens means being formed of synthetic rubber material through which the speed of ultrasound waves is substantially slower than the speed of ultrasound waves through soft tissue and having a convexly curved outer face for engagement with the skin covering the internal body matter toward which the ultrasound waves are transmitted, said convexly curved outer face including two portions one of which is larger and more gradually curved than the other portion and each of said portions being centered over the space between the first and second transducer means so that both portions extend partly over both transducer means, whereby the major portion of the ultrasound waves transmitted by the first transducer means pass through the larger, more gradually curved portion of the outer face of the lens means and are focused at a location spaced from the first transducer means and the smaller portion of the ultrasound waves transmitted by the first transducer means pass through the smaller, more sharply curved convex portion of the outer face of the transducer means and are focused at a distance from the first transducer means closer than the focusing of the ultrasound waves passing through the larger portion.

2. In the focusing mechanism defined in claim 1, the larger portion of the outer face of the lens means having a substantially constant radius of curvature at least twice as great as the maximum width of either transducer means.

3. In a focusing mechanism for a medical ultrasound device having first transducer means for transmitting ultrasound waves into the body toward internal body matter spaced from such transducer means and second transducer means for receiving at least some of the waves transmitted by the first transducer means which are reflected from such internal body matter, the improvement comprising lens means for refracting the ultrasound waves and having at least two curved portions each extending over portions of both of the transducer means, one of said curved portions having a radius of curvature much greater than the radius of curvature of the other curved portion, and one of the curved portions being much larger in area than the other curved portion for creating two focal zones, respectively, of substantial length at different distances from the first transducer means.

4. In the focusing mechanism defined in claim 3, the larger lens means curved portion having a radius of curvature much greater than the radius of curvature of the other lens means curved portion.

5. In the focusing mechanism defined in claim 3, the lens means curved portions being constructed and arranged relatively for creating two focal zones overlapping in range.

6. In the focusing mechanism defined in claim 3, the lens means being formed of a material through which the speed of ultrasound waves is substantially slower than 1500 meters per second, and both lens means curved portions being convex.

7. In the focusing mechanism defined in claim 3, the first and second transducer means having planar transmitting and receiving faces, respectively, the lens means having an inner face with planar portions butted against the planar transmitting and receiving faces of the transducer means, respectively, and both curved portions of the lens means being formed on the outer face of the lens means remote from the transducer means.

8. In the focusing mechanism defined in claim 3, the first and second transducer means being positioned in closely adjacent relationship with a gap therebetween, and the smaller lens means curved portion being approximately centered over the gap.

9. In the focusing mechanism defined in claim 8, both lens means curved portions being centered over the gap between the two transducer means.

10. In the focusing mechanism defined in claim 8, the lens means having an inner face adjacent to the transducer means and an outer face remote from the transducer means, and both lens means curved portions being formed on the outer face of the lens means.

11. In a focusing mechanism for an ultrasound device having first transducer means for transmitting ultrasound waves through a wave-conducting medium toward matter spaced from such transducer means and second transducer means for receiving at least some of the transmitted ultrasound waves after impinging on such matter, the improvement comprising converging lens means for refracting the ultrasound waves and having an inner face adjacent to the first transducer means and an outer face remote from the first transducer means, said outer face having at least two curved portions of substantially different curvature for focusing ultrasound waves transmitted by the transducer means at different distances, respectively, from the first transducer means, the first and second transducer means being positioned in closely adjacent relationship and both curved portions of the lens means extending over portions of both of the transducer means.

12. In the focusing mechanism defined in claim 11, one of the curved portions of the lens means being larger in area than the other curved portion of the lens means.

13. In the focusing mechanism defined in claim 12, the larger curved portion of the lens means having a radius of curvature much greater than the radius of curvature of the other curved portion of the lens means.

* * * * *